(12) United States Patent
Kamen et al.

(10) Patent No.: US 6,168,609 B1
(45) Date of Patent: Jan. 2, 2001

(54) CATAMENIAL COLLECTOR AND METHODS OF USE

(75) Inventors: Dean L. Kamen, Bedford; Larry B. Gray, Merrimack, both of NH (US)

(73) Assignee: Deka Products Limited Partners, Manchester, NH (US)

(*) Notice: Under 35 U.S.C. 154(b), the term of this patent shall be extended for 0 days.

(21) Appl. No.: 09/150,913

(22) Filed: Sep. 10, 1998

Related U.S. Application Data

(60) Provisional application No. 60/058,738, filed on Sep. 12, 1997.

(51) Int. Cl.[7] ................................................. A61M 29/00
(52) U.S. Cl. ........................ 606/193; 606/192; 604/317; 604/328; 600/573
(58) Field of Search ...................... 604/317, 327, 604/328, 329, 330, 96, 99, 103, 104; 606/192, 193, 195, 197, 198; 4/144.1, 144.4; 600/573, 574, 578, 579, 580

(56) References Cited

U.S. PATENT DOCUMENTS

| Re. 24,666 | 7/1959 | Draghi ................................. 128/285 |
| 923,303 * | 6/1909 | Shults . |
| 1,263,797 * | 4/1918 | Norquist . |
| 2,182,702 | 12/1939 | Previn ................................. 128/285 |
| 2,638,093 | 5/1953 | Kulick ................................. 128/133 |
| 2,905,169 | 9/1959 | Nieburgs ................................. 128/2 |
| 3,624,746 | 11/1971 | Grad et al. ......................... 128/285 |
| 3,850,160 | 11/1974 | Denson ................................. 128/2 B |
| 3,938,521 * | 2/1976 | Ritota et al. ....................... 604/329 |
| 3,939,838 | 2/1976 | Fujinami et al. ................. 128/290 R |
| 4,098,728 | 7/1978 | Rosenblatt ......................... 521/141 |
| 4,232,673 | 11/1980 | Bucalo ................................. 128/769 |
| 4,325,388 | 4/1982 | Bucalo ................................. 128/768 |
| 4,335,721 | 6/1982 | Matthews ........................... 128/285 |
| 4,486,191 | 12/1984 | Jacob ................................. 604/330 |
| 4,543,098 | 9/1985 | Wolfe et al. ....................... 604/370 |
| 4,747,166 * | 5/1988 | Kuntz ................................. 604/329 |
| 4,846,819 * | 7/1989 | Welch ................................. 604/329 |
| 5,002,541 * | 3/1991 | Conkling et al. ................... 604/319 |
| 5,061,187 | 10/1991 | Jerath ................................. 434/262 |
| 5,087,244 | 2/1992 | Wolinsky et al. ................... 604/53 |
| 5,122,407 | 6/1992 | Yeo et al. ........................... 428/138 |
| 5,167,237 | 12/1992 | Rabin et al. ....................... 128/748 |
| 5,188,630 | 2/1993 | Christoudias ....................... 606/1 |
| 5,209,754 * | 5/1993 | Ahluwalia ......................... 606/119 |
| 5,224,494 | 7/1993 | Enhorning ......................... 128/834 |
| 5,231,992 | 8/1993 | Leon ................................. 128/759 |
| 5,295,984 | 3/1994 | Contente et al. ................... 604/317 |
| 5,632,736 * | 5/1997 | Block ................................. 604/329 |
| 5,674,239 * | 10/1997 | Zadini et al. ....................... 606/193 |
| 5,772,645 | 6/1998 | Zadini et al. ....................... 604/358 |
| 5,795,288 * | 8/1998 | Cohen et al. ....................... 600/29 |
| 5,827,248 | 10/1998 | Crawford ........................... 604/328 |
| 5,893,176 * | 4/1999 | Magiera et al. ................... 604/329 |
| 5,947,992 * | 9/1999 | Zandini et al. ..................... 606/193 |

FOREIGN PATENT DOCUMENTS 351654   4/1922   (DE) .

OTHER PUBLICATIONS

International Search Report for PCT US98/18781 which cites references AA, AB, AS, and AY.

* cited by examiner

Primary Examiner—John G. Weiss
Assistant Examiner—David J. Cho
(74) Attorney, Agent, or Firm—Bromberg & Sunstein LLP

(57) ABSTRACT

A catamenial collector, in an embodiment, has a receptacle with a flexible hollow rim capable of inflation and has a handle with substantially the length of a female vagina. The collector may have a string, in one embodiment, extending through the rim and at least a portion of the handle so that a pulling force axially applied to a string end causes the receptacle to close. In another embodiment, an elastic member is so configured that deflation of the rim also causes the receptacle to close. The collector and associated methods of use provide for the sanitary collection and disposal of menses.

35 Claims, 4 Drawing Sheets

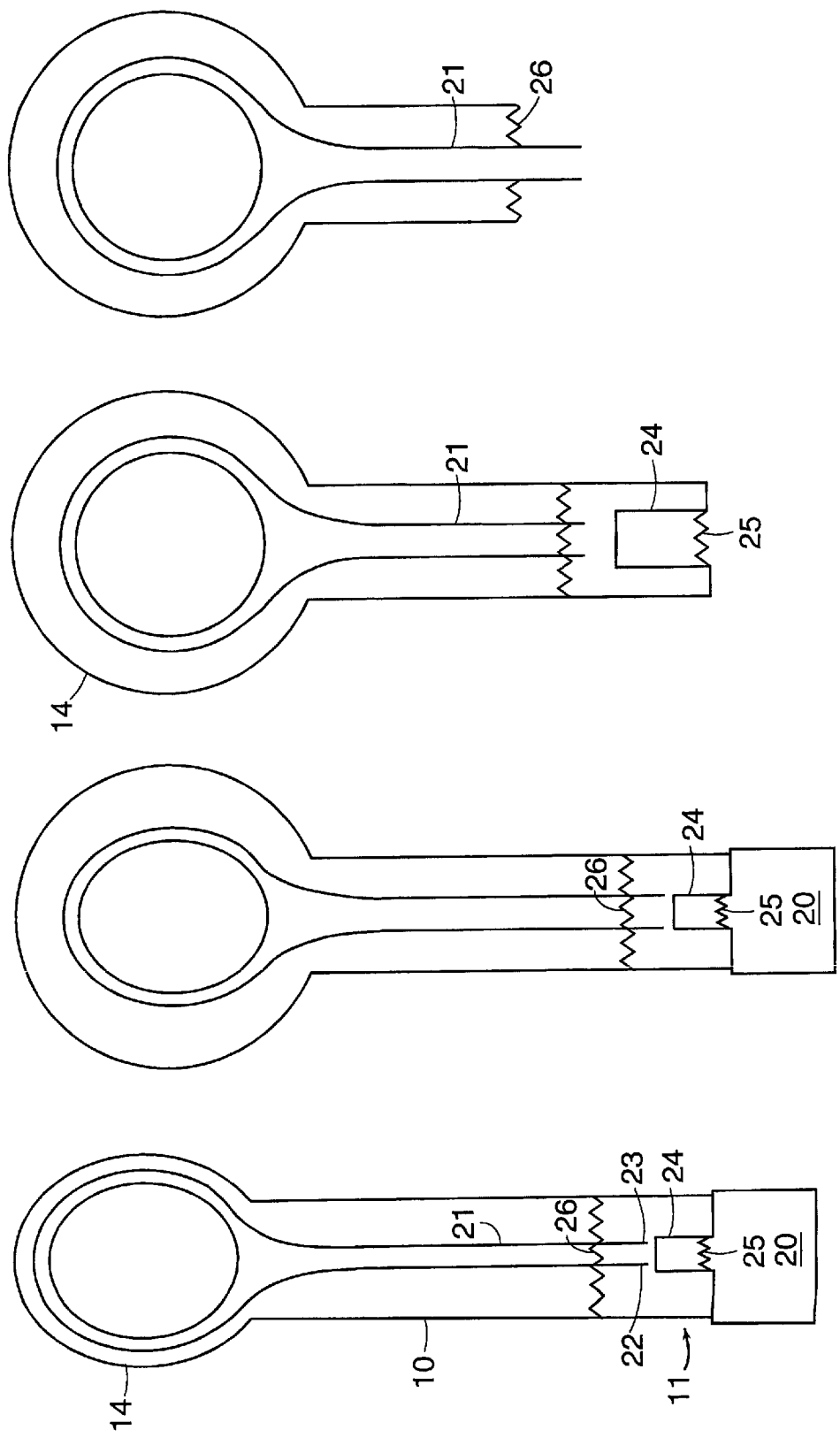

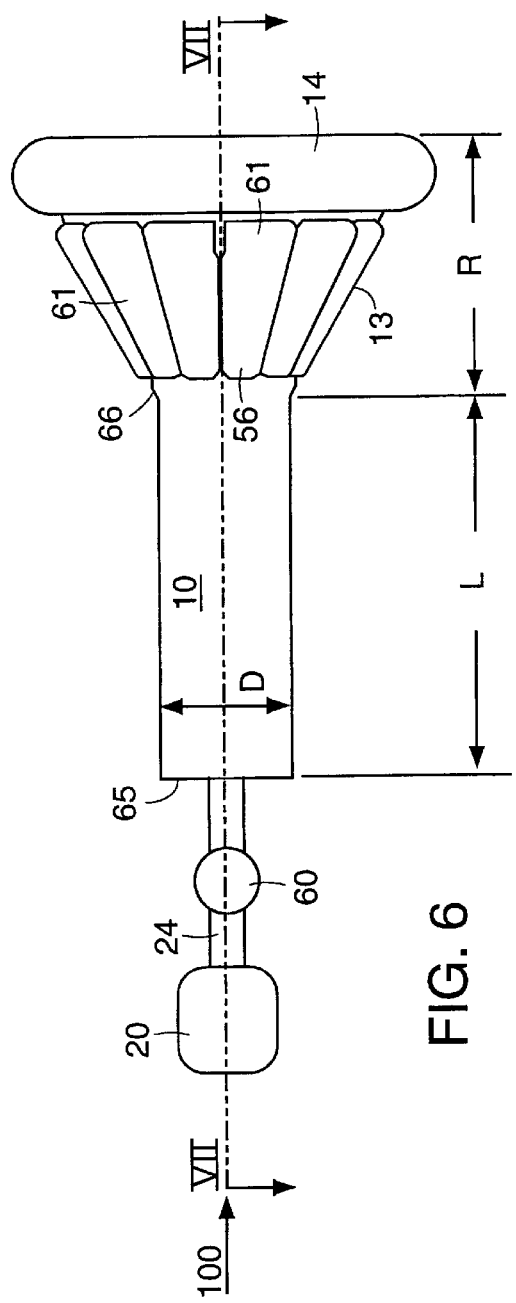
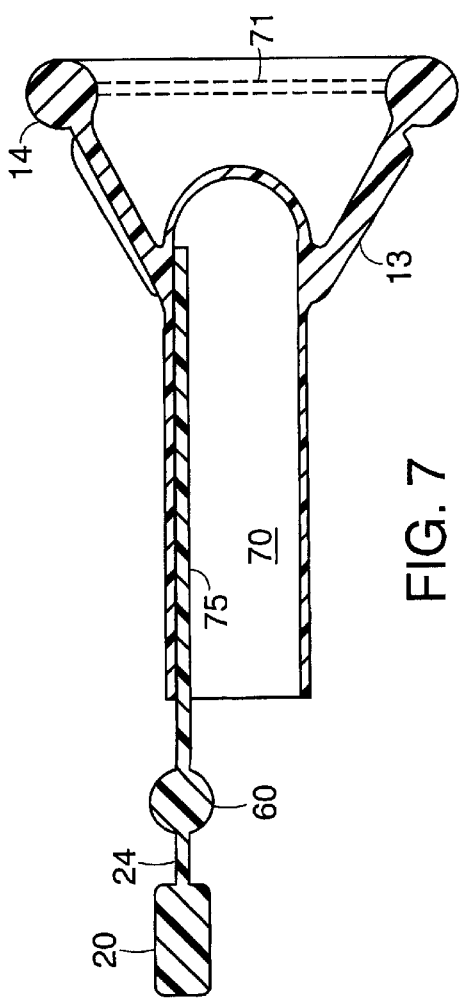
FIG. 6
FIG. 7

CATAMENIAL COLLECTOR AND METHODS OF USE

RELATED U.S. APPLICATION(S)

This application claims priority from U.S. Provisional Application Ser. No. 60/058,738, filed Sep. 12, 1997, which is hereby incorporated herein by reference.

TECHNICAL FIELD

The present invention relates to devices used to collect catamenial flow during menstruation.

BACKGROUND ART

The majority of women utilize devices during the menstrual cycle to collect blood flow. One type of collector is an externally placed absorbent pad, napkin or shield. These tend to be bulky and retain undesirable odor. Two other device types are placed internally. The first of these is a tampon in the form of an absorbent (usually cotton) plug for placement inside the vaginal cavity. The other is a cervical cup having a flexible ring formed from a rigid polymer. The ring supports a cup which is formed from a thin impermeable layer of a polymer which is open on top. Such internal devices have numerous disadvantages.

The typical tampon currently used by women to absorb the flow of menses consists of a cotton plug, 1½ to 3½ inches in length with a cotton string threaded through the plug and extending from one end. The tampon is introduced into the vaginal cavity either manually or by means of an applicator which is removed after insertion. With either method, the string extends outside the vaginal cavity and is subsequently used for tampon removal.

The use of tampons has been linked to Toxic Shock Syndrome. A toxin produced by *Staphylococcus aureus* is known to cause serious illness. One theory for the cause of this syndrome is that the string associated with the absorbent plug has the properties of a wick and may act as a conduit for harmful bacteria migrating from outside of the body into the membranes of the vaginal cavity. Another theory is that the absorbency of the plug itself or, alternatively, the increased incidence of infection at the site of abraded or desiccated vaginal membranes damaged as a consequence of the insertion, maintenance and removal of a tampon from the vagina. The abrasive effect of the tampon on the vaginal membranes is believed to arise both upon placement of an unmoistened plug in the vagina and when an enlarged moist plug is dragged out of the vagina by means of the string. Furthermore, over absorbency that is created in the plug to reduce its initial size may result in absorption of normal vaginal membrane secretions leading to desiccation and further damage to the membrane.

The cervical cup is inserted by compressing and pushing the flexible hard plastic ring attached to a non permeable cup to the end of the vagina. The cup is removed after 12 hours by inserting a finger and pulling the cup out. A disadvantage of this device is the inconvenience of inserting a finger into a bloodied vagina. Furthermore, the contents of the cup holding the catamenial fluid, may spill resulting in an undesirable mess. In addition, this device is not suitable for flushing down a toilet. U.S. Pat. No. 5,295,984 to Contente et al. discloses such a cervical cup used as a vaginal discharge collector and claims methods of using such a device.

Recently, U.S. Pat. No. 5,674,239 and related U.S. Pat. No. 5,772,645 to Zadini et al. disclose an intravaginal balloon and a balloon associated with absorbent material for use in the vaginal cavity.

SUMMARY OF THE INVENTION

Various embodiments of the present invention solve problems of the prior art. Preferred embodiments provide devices having sufficient capacity to be effective in collecting catamenial fluid for 12 hours and offer sanitary insertion into and sanitary retrieval from a woman's anatomy. Preferred embodiments provide the capability to transport the collector in a clothing pocket.

Accordingly, in a first embodiment of the invention there is provided a catamenial collector having a receptacle and a handle. The receptacle has a flexible hollow rim which has a port for the introduction of an inflation fluid. The handle has a length which defines an axis and substantially the length of a vagina. The handle has a fluid channel disposed along the length in fluid communication with the port so as to facilitate inflation of the rim. Further, the collector may have a string extending through the rim and at least a portion of the handle so that a pulling force axially applied to a string end causes the receptacle to close. A collector may have a pump for inflating the rim. The pump, in accordance with an embodiment is in fluid communication with the fluid channel and is coupled proximate to the second end. The collector may further have a valve axially disposed within the handle between and in fluid communication with the pump and the rim. Preferably, a tear site is axially disposed between the pump and the valve in order to facilitate removal of the pump when in use. The string end, in accordance with an embodiment, is not exposed and is not available to cause an undesirable wicking effect while the collector is in use. The collector may have a second tear site axially disposed between the valve and the rim, so that the valve may be removed so as to expose the string end and deflate the rim. In a further embodiment, the collector has an elastic member so configured that deflation of the rim also causes the receptacle to close. The collector is capable of being compressed into a volume substantially less then the volume it occupies when the rim is inflated.

In another embodiment of the invention, the collector has a handle with a coupling end, a receptacle with both a closed end and a second fluid channel, so that the coupling end is attached to the closed end and the fluid channel, the second fluid channel, and the port are in fluid communication with each other. It may further include an elastic member so configured that deflation of the rim also causes the receptacle to close. A further embodiment has a collapsible application tube coupled to and oriented coaxially with the handle. The application tube is biased towards a collapsed state. In accordance with an embodiment of the invention, the handle may have a second end and a pump for inflating the rim. The pump is in fluid communication with the fluid channel facilitating inflation of the rim and is coupled proximate to the second end. The collector may further have a valve axially disposed within the handle between and in fluid communication with the pump and the rim. Still further, it may have a tear site axially disposed between the pump and the valve. In addition, the collector may have a reservoir axially disposed between and in fluid communication with the valve and the rim to remotely indicate whether the rim is in an inflated condition.

Another embodiment of the present invention provides a method for the sanitary collection and disposal of menses having the steps of:

providing a catamenial collector along the lines of one of the aforementioned embodiments;

inserting the collector into the vagina; and inflating the collector's rim such that the rim contacts and forms a fluid-tight seal with vaginal walls.

After an effective collection time, the collector's handle may be grasped, and the collector removed from the vagina.

BRIEF DESCRIPTION OF THE DRAWINGS

FIG. 2 is a top view of an embodiment of a catamenial collector prior to insertion according to an embodiment of the invention.

FIG. 3 is a top view of an embodiment of a catamenial collector after rim inflation.

FIG. 4 is a top view of an embodiment of a catamenial collector after insertion and pump removal.

FIG. 5 is a top view of an embodiment of a catamenial collector after valve removal just prior to rim deflation.

FIG. 6 is a longitudinal view of another embodiment of a catamenial collector.

FIG. 7 is a cross-sectional view of a catamenial collector shown in FIG. 6, along line VII—VII.

DETAILED DESCRIPTION OF SPECIFIC EMBODIMENTS

Figure 1:
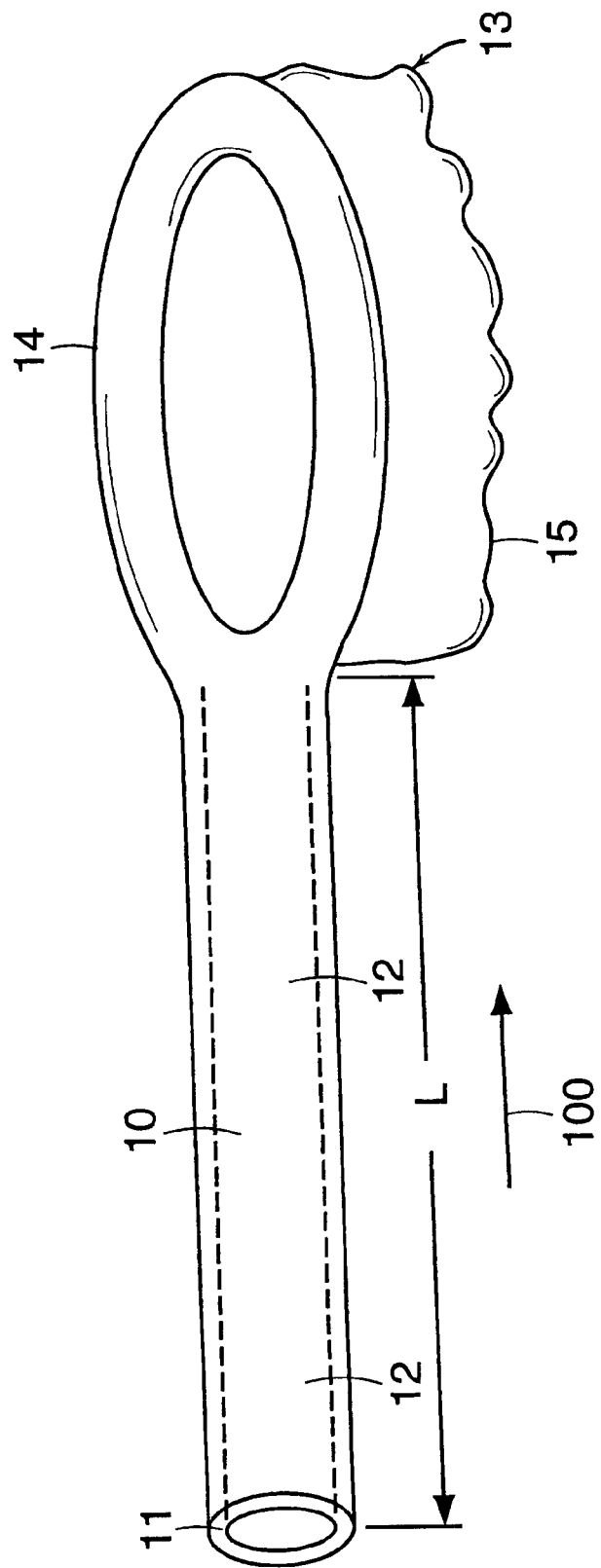
FIG. 1 is a side view of a catamenial collector as configured when functioning within a woman's vaginal cavity according to an embodiment of the invention.

FIG. 1 is a side view of the catamenial collector as configured when functioning within a woman's vaginal cavity according to an embodiment of the invention. During operation, the collector extends from the cervical opening, where collection occurs, along the length of the vagina with the possibility of extending beyond the vaginal cavity. Handle 10 defines an axis represented by arrow 100. The length, L, of handle 10 is at least the length of a vagina so that the user may grasp end 11 while the collector is in use or is being positioned for use. The handle 10 has a fluid channel 12 disposed along its length, running from a location proximal to end 11 to an opposing end near the catamenial collection site. The handle 10 is in fluid communication with a receptacle 13 via fluid channel 12. The receptacle 13 has a flexible rim 14. The rim 14 is hollow and inflatable. Fluid communication is accomplished through the mating of a port disposed in the rim 14 with fluid channel 12. During operation, inflated rim 14 provides a fluid-tight seal between the receptacle 13 and the vaginal wall surrounding the cervical opening allowing the sanitary collection of catamenial fluid during menstruation. The bag-like portion 15 of the receptacle expands to accept fluid. The portion 15 is designed to provide the capability of twelve hours of continual catamenial fluid collection before removal of the collector. In another embodiment, the handle 10 is also capable of inflation via fluid channel 12. This capability would allow a user to carry the collector prior to use in a substantially compressed condition and stored in a small pouch. At time of use, the collector may be removed from the storage container and inflated with air. Polymeric materials which are compressible, impermeable, flexible, and lightweight are preferred candidates for use in the catamenial collector.

FIGS. 2–5 are top views of an embodiment of the catamenial collector viewed at various times. Inflation may occur through use of a detachable pump 20 located at end 11 of handle 10. Prior to inflation, according to an embodiment with an inflatable handle 10, the pump 20 is attached to a deflated polymeric inflatable portion. The pre-use storage volume is therefore only slightly greater than that of the pump 20. FIG. 2 shows the collector with the handle 10 inflated or, otherwise, in position for use. The rim 14 is shown with a circular shape but may be any other shape suitable for effectively sealing with the vaginal wall surrounding the cervical opening so as to collect fluid. At least one string 21 may be placed within the handle 10, fed through the fluid channel and the port into the rim 14 such that it forms a loop throughout the rim 14 and so that both string ends 22 and 23 terminate in the handle 10. Alternatively, a lasso-type configuration for the string 21 may be utilized resulting in a single end within the handle 10. The end(s) of the string 21 may be separated from contact with the pump by a one-way valve 24. Embodiments of the invention may utilize any of a selection of different types of valves including duckbilled valves. Furthermore, a tear mark 25 may be positioned below the one-way valve 24 and the pump 20 so as to allow the pump 20 to be removed from the catamenial collector after satisfactory inflation has been achieved. To install, the user flexes the inflated rim 14 and places the collector into the vagina. FIG. 3 shows the collector after it is positioned within the vaginal cavity with the rim 14 aligned to seal with the vaginal walls and to permit catamenial fluid to enter the receptacle. Adjustments to the turgidity of the inflated rim 14 may be made by the user via the pump 20 to improve comfort during use. The device may stay in place for 12 hours. FIG. 4 shows the collector after removal of the pump 20 at tear mark 25. A second tear mark 26 may be placed between the valve 24 and the rim 14 so as to permit removal of a piece of the handle 10, thereby exposing the end(s) of the string 21 for use during withdrawal of the collector. FIG. 5 illustrates the collector in this condition in accordance with this embodiment. As one-way valve 24 has been removed from the collector, the rim 14 will deflate breaking the seal with the vaginal walls. Concurrently, an axial pulling force applied to the string 21 will cause the receptacle to close, entrapping the fluid. The string 21 and handle 10 may be grasped and the collector removed from the vaginal cavity in a sanitary manner. Despite the use of a string 21, the embodiment avoids wicking action as the ends do not remain exposed during use. In addition, damage to the vaginal membranes from abrasion or desiccation is minimized because of the smooth polymeric materials of construction.

FIGS. 6 and 7 are longitudinal and cross-sectional views, respectively of another embodiment of the catamenial collector. This embodiment of the collector features the rim 14, the receptacle 13, and the handle 10 each having axis 100 as a common axis of symmetry. As shown in FIG. 6, the handle 10 has a coupling end 66 while the receptacle has a closed end 56. Fluid channels 61 provide fluid communication between the fluid channel 75 disposed in the handle 10 (shown in FIG. 7). Inflation may occur through use of a detachable pump 20 located proximal to a second end 65 of handle 10. Inflation fluid flows through the pump 20, through fluid channels 75 and 61 into rim 14 FIG. 7 shows an elastic member 71 which maintains the receptacle 13 to be closed until rim 14 is inflated. A reservoir 60 is, according to an embodiment, interposed in the inflation pathway between the pump 20 and the fluid channel 75 to remotely indicate whether the rim is in an inflated condition. A one-way valve 24 is shown disposed between the pump 20 and the reservoir 60. The handle 10, as shown in cross-section, provides a collapsible application tube 70. A user's finger or other applicator, when inserted into tube 70, guides the collector into or out of the vaginal cavity of the user offering a sanitary method of use. The tube 70 is made of polymeric material and designed so that it collapses with the removal of the applicator. In this embodiment of the invention, the collector may be efficiently inserted prior to the inflation of rim 14. When the collector is ready to be removed from the cavity, the valve 24 may be removed and the rim 14 deflated. The elastic member 71 serves to close the receptacle 13 upon deflation of the rim 14, thus sealing the catamenial fluid inside the receptacle 13. The collector may then be removed from the cavity without undue risk of fluid spillage. As with other embodiments described above, tear marks or other suitable assistance in removing the pump 20 during use may be included with the collector in accordance with an embodiment of the invention. Typical dimensions of fabricated collectors are approximately 25 mm for the diameter D of handle 10, 68 mm for the length L of handle 10, and 46 mm for the depth R of the receptacle 13. Fabrication methods for making such collectors are well known in the art and include dip molding and injection molding.

Figure 8:
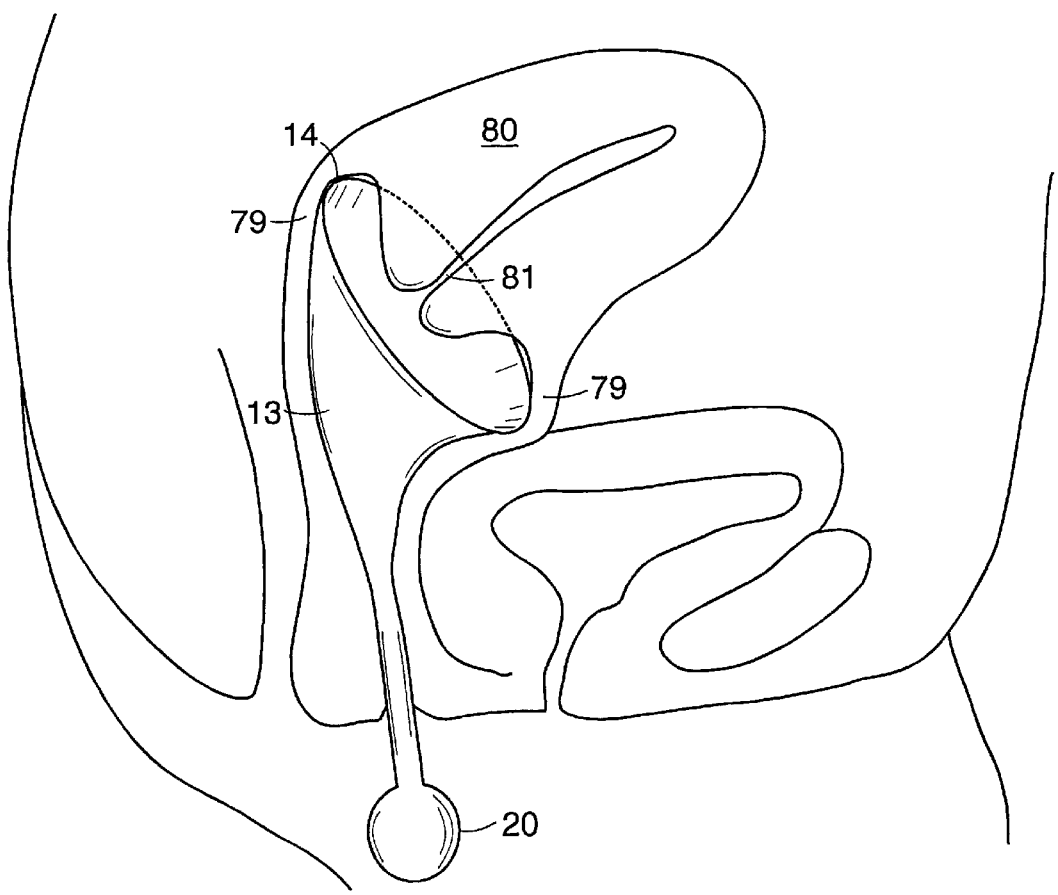
FIG. 8 is a schematic representation of a catamenial collector, in accordance with an embodiment of the invention, situated in the vaginal cavity of a user, shown within a cross-section of the pelvic region.

FIG. 8 is a schematic representation of a catamenial collector situated within the vaginal cavity of a user. In accordance with an embodiment of the invention, an inflated rim 14 forms a seal with vaginal walls 79 surrounding a cervical opening 81 (the cervix denoted as 80) so that spill-free collection of catamenial fluid occurs. The receptacle 13 is capable of continually collecting catamenial fluid over a twelve hour time span. Pump 20 is shown in position external to the body of the user. As described above, a valve may be included in line between the pump 20 and the receptacle 13 so that the rim may remain inflated after pump 20 is removed from the collector.

Although the invention has been described with reference to several preferred embodiments, it will be understood by one of ordinary skill in the art that various modifications can be made without departing from the spirit and the scope of the invention, as set forth in the claims hereinbelow.

What is claimed is:

1. A collector for collecting and retaining catamenial fluid comprising:
    a handle having a coupling end, a second end, and a length, the length substanitally that of a vagina, the length defining an axis, the handle having a fluid channel disposed along the length, wherein the handle is unexposed to the catamenial fluid; and
    a receptacle having a closed end, the closed end of the receptacle coupled to the handle proximal to the coupling end, the receptacle having a flexible hollow rim, the rim having a port;
wherein the fluid channel is in fluid communication with the port so as to facilitate inflation of the rim.

2. A collector according to claim 1, further comprising:
    a string extending through the rim and at least a portion of the handle.

3. A collector according to claim 2, wherein the string forms a loop throughout the rim and a string end is located in the handle.

4. A collector according to claim 3, wherein the string and the rim are so configured that a pulling force axially applied to the string end causes the receptacle to close.

5. A collector according to claim 3, wherein the handle having a first end and a second end, the collector further comprising:

a pump for inflating the rim,
the pump in fluid communication with the fluid channel and coupled proximate to the second end.

6. A collector according to claim 5, further comprising:
    a valve axially disposed within the handle between and in fluid communication with the pump and the rim.

7. A collector according to claim 6, further comprising:
    a tear site axially disposed between the pump and the valve.

8. A collector according to claim 7, further comprising:
    a second tear site axially disposed between the valve and the rim, so that the valve may be removed so as to expose the string end.

9. A collector according to claim 1, capable of being compressed into a reduced volume substantially less than a volume the collector occupies when the rim is inflated.

10. A collector according to claim 1, further comprising:
    an elastic member, so configured that deflation of the rim also causes the receptacle to close.

11. A collector according to claim 1, further comprising:
    a pump for inflating the rim, the pump in fluid communication with the fluid channel and coupled proximal to the second end.

12. A collector according to claim 11, further comprising:
    a valve axially disposed within the handle between and in fluid communication with the pump and the rim.

13. A collector according to claim 12, further comprising:
    a tear site axially disposed between the pump and the valve.

14. A collector according to claim 1, the receptacle having a closed end and a second fluid channel, wherein the coupling end is attached to the closed end and the fluid channel, the second fluid channel, and the port are in fluid communication with each other.

15. A collector according to claim 14, further comprising:
    an elastic member, so configured that deflation of the rim also causes the receptacle to close.

16. A collector according to claim 15, further comprising:
    a collapsible application tube,
the tube coupled to and oriented coaxially with the handle, the tube being biased collapsed.

17. A collector according to claim 15, further comprising:
    a pump for inflating the rim, the pump in fluid communication with the fluid channel and coupled proximal to the second end.

18. A collector according to claim 17, further comprising:
    a valve axially disposed within the handle between and in fluid communication with the pump and the rim.

19. A collector according to claim 18, further comprising:
    a tear site axially disposed between the pump and the valve.

20. A collector according to claim 18, further comprising:
    a reservoir axially disposed between and in fluid communication with the valve and the rim.

21. A collector for collecting and retaining catamenial fluid, the collector and catamenial fluid adapted to fit inside and remain within a vaginal cavity for an extended time period, the collector comprising:
    a receptacle having a closed end and having a flexible hollow rim, the rim having a port; and
    a handle having a length, the length substantially that of a vagina, the length defining an axis, the handle coupled to the receptacle proximal to the closed end of the receptacle and having a fluid channel disposed along the length; wherein the fluid channel is in fluid communication with the port so as to facilitate inflation of the rim, and wherein the handle is, essentially, unexposed to catamenial fluid.

22. A collector according to claim 21, wherein the extended time period is twelve hours.

23. A collector according to claim 21, capable of being compressed into a volume substantially less then the volume the collector occupies when the rim is inflated.

24. A collector according to claim 21, further comprising:
an elastic member, so configured that deflation of the rim also causes the receptacle to close.

25. A collector according to claim 21, wherein the handle has a coupling end and a second end, the receptacle coupled to the handle proximal to the coupling end, the collector further comprising:
a pump for inflating the rim, the pump in fluid communication with the fluid channel and coupled proximal to the second end.

26. A collector according to claim 25, further comprising:
a valve axially disposed within the handle between and in fluid communication with the pump and the rim.

27. A collector according to claim 26, further comprising:
a tear site axially disposed between the pump and the valve.

28. A collector according to claim 21, the receptacle having a closed end, the handle having a coupling end, a second end and a second fluid channel, wherein the coupling end is attached to the closed end and wherein the fluid channel, the second fluid channel, and the port are in fluid communication with each other.

29. A collector according to claim 28, further comprising:
an elastic member, so configured that deflation of the rim also causes the receptacle to close.

30. A collector according to claim 29, further comprising:
a collapsible application tube,
the tube, coupled to and oriented coaxially with the handle, the tube being biased collapsed.

31. A collector according to claim 29, further comprising:
a pump for inflating the rim, the pump in fluid communication with the fluid channel and coupled proximal to the second end.

32. A collector according to claim 31 further comprising:
a valve axially disposed within the handle between and in fluid communication with the pump and the rim.

33. A collector according to claim 32, further comprising:
a tear site axially disposed between the pump and the valve.

34. A collector according to claim 31, further comprising:
a reservoir axially disposed between and in fluid communication with the valve and the rim.

35. A collector according to claim 21, wherein the handle, during the extended time period, is unexposed to catamenial fluid.

* * * * *